United States Patent [19]
Fisk et al.

[11] Patent Number: 5,257,650
[45] Date of Patent: Nov. 2, 1993

[54] TWO-PIECE REAGENT CONTAINER ASSEMBLY

[75] Inventors: Richard Fisk, Granada Hills; James Miller, Arcadia, both of Calif.

[73] Assignee: Abbott Laboratories, Abbott Park, Ill.

[21] Appl. No.: 940,601

[22] Filed: Sep. 4, 1992

Related U.S. Application Data

[62] Division of Ser. No. 360,653, Jun. 2, 1989, Pat. No. 5,152,965.

[51] Int. Cl.⁵ .............................................. B65B 1/04
[52] U.S. Cl. ...................................... 141/9; 141/319; 141/363; 141/364
[58] Field of Search ............... 141/319, 320, 321, 322, 141/323, 363, 364, 365, 366, 375; 422/102, 103, 104; 206/219, 221, 222; 435/206, 300; 604/82, 87, 89, 91, 416, 905

[56] References Cited

U.S. PATENT DOCUMENTS 3,684,455  8/1972  Vacirca et al. ..................... 206/219
3,917,063  11/1975  Chisret et al. ..................... 141/329
4,784,658  11/1988  Grasenkort ......................... 604/416

Primary Examiner—Henry J. Recla
Assistant Examiner—David J. Walczak
Attorney, Agent, or Firm—Gregory W. Steele; Thomas M. Breininger

[57] ABSTRACT

An assembly of containers is provided for efficient and controlled storage of a reagent and subsequent mixing of the reagent with a reagent diluent. The assembly includes a reagent diluent container and a sealed reagent vial. An adapter assembly includes a coupler having one end mountable to the reagent diluent container and having the opposed end defining a hollow plunger. A retainer ring has one end mountable to the coupler and the opposed end mountable to the reagent vial. The reagent vial is engageable with the coupler in a first position and is advanceable into a second position relative to the adapter assembly such that the hollow plunger thereof displaces the seal of the reagent vial permitting the reagent in the reagent vial to flow through the hollow plunger to mix with a buffer or diluent in the reagent diluent container.

5 Claims, 3 Drawing Sheets

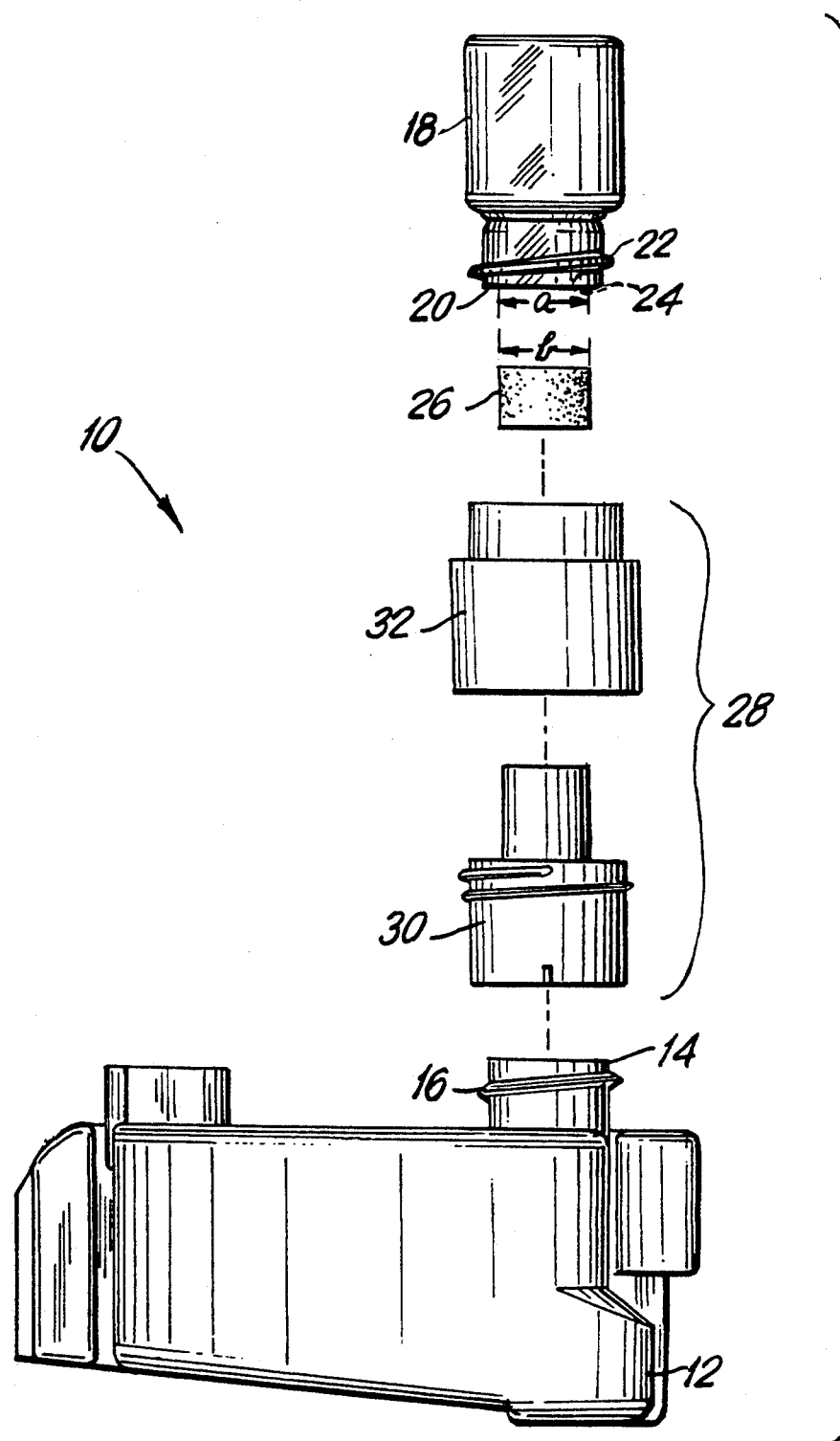
FIG. I

TWO-PIECE REAGENT CONTAINER ASSEMBLY

This is a division, of application Ser. No. 07/360,653, filed Jun. 2, 1989, now U.S. Pat. No. 5,152,965.

BACKGROUND OF THE INVENTION

Hospitals and clinical laboratories perform many clinical chemical analyses on blood, urine or other body fluids. The analyses may be conducted to determine levels of cholesterol, glucose, triglycerides, bilirubin and the like Tests may also be conducted to identify the presence and/or level of certain components such as calcium or phosphorus in body fluids. Other tests may be performed to identify the presence and/or level of hormones.

Clinical chemical laboratories generally are required to provide a plurality of different test results for each sample submitted for analysis. In particular, the laboratory may be requested to identify levels of cholesterol, LDH, HBDH and triglycerides from the blood sample for a particular patient. A complete laboratory work-up may involve tests to identify levels of many more substances. Diagnostic tests for each substance generally must be carried out separately by the clinical chemical laboratory. In particular, the test for each substance is carried out by presenting a controlled portion of the sample submitted for analysis to a particular reagent. The amount of the sample and the amount and type of reagent will vary depending upon the particular substance being tested for. A complete clinical laboratory work-up may involve dividing a blood sample into twenty different parts which are then mixed in twenty different reagent containers for analysis.

Most clinical chemical analysis has been substantially automated. In particular, the samples to be tested may be stored in opened containers which are accessed by robotic probes which advance into the liquid sample, withdraw a specified amount of the sample, and deliver the sample to a reagent container. The reagent may be selected to enable a colormetric test. In particular, the reagent with the sample therein may produce a color when subjected to electromagnetic excitation. The particular color produced may be identified by polychromatic optical sensors which are operative to identify the wave length of light passed through the reagent with the sample therein. The specific wave length sensed by the polychromatic optical sensor is then employed to identify either the presence or level of the substance being tested for. The equipment used to perform these diagnostic tests may also be operative to read bar codes or color codes to identify the patient sample, and to identify the particular substance and reagent being tested for.

The reagent employed to complete each test generally is produced by mixing a concentrated reagent in liquid or powder form with a diluent or buffer. The type of diluent or buffer being employed will depend in part upon the reagent and the substance being tested for in the sample. In some instances the diluent or will be water or a buffer. The powder or concentrated liquid reagent generally will have a fairly long useful life. However, the life will be shortened substantially after the concentrated reagent is mixed with the diluent.

Additionally, the storage requirements may vary depending upon the particular mixture of reagent and diluent. Some diluted reagents may require refrigeration, while others may require storage at room temperature. These various storage requirements for the combined reagent/diluent create tremendous inventory control problems. Improperly stored mixtures can result in inaccurate test results. In view of these inventory and storage problems, many clinical chemical laboratories defer mixing the concentrated reagents with the diluent or buffer until shortly prior to the actual performance of tests. This inherently requires on-site mixing of the reagent and the diluent or buffer. Such on-site mixing of reagents has several disadvantages, including the time required for laboratory technicians to perform the mixing and the significant possibility of incorrect proportions or contamination, either of which could substantially affect the test results. Additionally, this need to mix reagents and diluents or buffers shortly prior to performing tests can force clinical chemical laboratories into less than optimum testing schedules. In particular, the laboratories may be forced into routines where they will test a plurality of different samples for one substance to enable the reagent required for that substance to be used shortly after mixing. This can result in a longer turn around time to produce a complete test report for each patient/sample and can add to the complexities of matching test results to patient samples.

In view of the above, it is an object of the subject invention to provide containers for facilitating the mixing of reagents with diluents or buffers.

It is another object of the subject invention to provide reagent containers that eliminate on-site measuring of reagents and diluents at the clinical laboratory.

A further object of the subject invention is to provide reagent containers that minimize inventory control problems for reagents and diluents.

Still another object of the subject invention is to provide an apparatus to enable precise mixing of reagents and diluents or buffers immediately prior to performing tests therewith.

SUMMARY OF THE INVENTION

The subject invention is directed to an assembly of containers and to an adapter for selectively placing first and second containers in communication with one another. The first and second containers preferably each comprise attachment means for enabling attachment of the adapter assembly thereto. The first container may define a reagent buffer container or a reagent diluent container having an opening formed therein with the attachment means adjacent or unitary with the opening. The second container may define a reagent vial for storing a concentrated liquid or powder reagent to be mixed with the buffer or diluent. The second container may be formed from glass or plastic depending upon the characteristics of the reagent stored therein. In particular, a powder reagent typically will require the second container to be formed from glass to prevent intrusion of moisture therein. Many concentrated liquid reagents may be stored in second containers formed from suitable plastic material. The second container also comprises an opening having attachment means for selectively receiving the adapter assembly thereon. For example, external portions of the second container adjacent the opening therein may be provided with an array of external threads. The second container also preferably is provided with sealing means for securely and positively sealing the reagent or other such contents of the second container. Many reagents are highly caustic and may react with the seal extending across the opening therein. Therefore, in the preferred embodiment the seal will define a stopper securely urged into the opening of the second container. However, it is envisioned that in certain embodiments a thin frangible seal of, for example, foil or plastic film may extend across the opening in the second container.

The adapter is selectively mountable to both the first and second containers. For example, the adapter may comprise opposed ends with arrays of threads that are selectively engageable with corresponding arrays of threads on the first and second containers. The adapter further comprises communication means for providing communication between the first and second containers to enable the mixing of the contents of the respective first and second containers.

The adapter may further comprise means for displacing a seal on at least one of the first and second containers. In particular, the adapter may comprise a plunger that is spaced from the mounting means and that may be selectively movable relative to other portions of the adapter. The adapter may thus be employed to enable selective displacement of a seal on at least one of the containers. In a preferred embodiment, a plunger provided on the adapter is operative to selectively displace a stopper or frangible seal disposed in or extending across the opening of the second container. The plunger may be hollow to define at least a portion of the communication means.

A preferred embodiment, as explained in detail below, comprises an adapter assembly formed from a plurality of selectively engageable components. A first component of the adapter assembly may have opposed first and second ends. The first end of this first component may be selectively engageable with the opening in the first container. The opposed second end of the first component of the adapter assembly may define a plunger which is selectively urgeable into the seal of the second container to displace the seal as explained herein. The second component of the adapter assembly may also comprise opposed first and second ends. The first end of this second component of the adapter assembly may be selectively engageable and movable relative to the first component thereof. The opposed second end of the second component of the adapter assembly may be selectively engageable with the opening in the second container. The interengagement between the first and second components of the adapter assembly may define mateable threads which enable the first and second components of the adapter assembly to be selectively advanced or retracted relative to one another.

In use, the second container may be provided with a reagent or other such material stored therein with a seal being disposed in or across the opening to the second container. The first and second components of the adapter assembly may then be initially engaged with one another. The second component of the adapter assembly may be attached to the second container such that the plunger of the first component of the adapter assembly is in proximity to the seal of the second container. The mounting of the first and second components of the adapter assembly is such that a further advancement of the first and second components toward one another will displace the seal of the second container. The second container with the reagent or other such contents securely sealed therein may have the adapter assembly mounted thereto by the manufacturer of the reagent. This assembly of a precisely measured and sealed concentrated reagent is packaged under carefully controlled conditions by the manufacturer. Additionally, the concentrated reagent liquid or powder can be stored in this sealed condition for a relatively long duration.

A reagent diluent, such as water or buffer may be stored in the first container, or may be placed in the first container immediately prior to conducting selected clinical chemical analysis. Prior to conducting the analysis, the laboratory technician may take an appropriate second container having the reagent stored therein and the adapter assembly mounted thereon. The technician may attach the first end of the first component of the adapter assembly to the opening in the first container. The technician may then twist or otherwise advance the first and second containers toward one another such that the first and second components of the adapter assembly further advance into engagement with one another. Sufficient advancement in this manner will cause the plunger of the first component of the adapter assembly to displace the seal on the second container and enable the mixing of the contents of the first and second containers. In the typical embodiment where the seal in the second container defines a stopper, the plunger is operative to advance the stopper entirely into the second container. This movement of the stopper into the second container, in response to forces generated by the plunger, may create a turbulence therein to urge the contents of the second container into the first container. The connected containers may be inverted to ensure complete flushing of the reagent.

After the contents of the first and second containers have been mixed, the adapter assembly and the second container may be removed from the first container to enable appropriate testing to be carried out on the combined contents. The testing may be carried out on known clinical chemical diagnostic equipment as explained above.

BRIEF DESCRIPTION OF THE DRAWINGS

FIG. 1 is an exploded side elevational view of a container assembly in accordance with the subject invention.

DETAILED DESCRIPTION OF THE PREFERRED EMBODIMENTS

Figure 3:
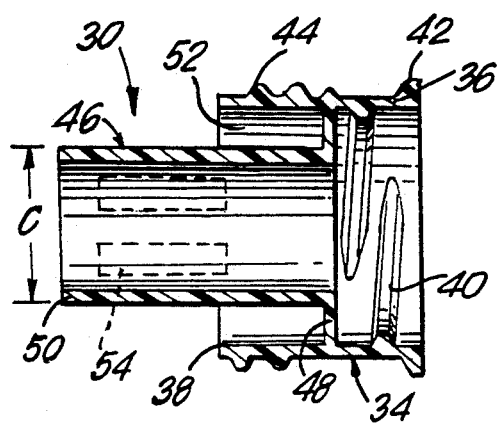
FIG. 3 is a cross sectional view taken along line 3—3 in FIG. 2.

The container assembly of the subject invention is identified generally by the numeral 10 in FIG. 1. The container assembly 10 comprises a reagent diluent container 12 which may blow molded from a suitable plastic material and which is configured for placement in an appropriate clinical chemical testing apparatus such as the ABBOTT SPECTRUM ® diagnostic testing system. The reagent diluent container 12 includes an opening 14 defining a neck extending upwardly from the reagent diluent container 12. The opening neck 14 is characterized by an array of external threads 16 formed thereon. The opening 14 permits the addition of an appropriate reagent diluent, such as water, sterile water, saline, phosphate-buffered saline, TRIS or TWEEN buffers or the like, into the reagent diluent container 12.

The assembly 10 shown in FIG. 1 further comprises a reagent vial 18 which may be blow molded or injected molded from a suitable plastic or which may be formed from glass. Generally the reagent vial 18 will be formed from glass for storing powdered reagents which may be susceptible to the intrusion of moisture that conceivably could migrate through certain plastics. On the other hand, the reagent vial 18 may be formed from a suitable plastic for storing concentrated liquid reagents therein. The reagent vial 18 includes an opening 20 defining a neck having an array of external threads 22 thereon. The internal surface 24 of the opening neck 20 defines a generally smooth cylindrical surface of diameter "a". The reagent vial 18 is used in conjunction with an elastomeric stopper 26 which is of cylindrical configuration and defines an external diameter "b" which preferably is equal to or slightly greater than the internal diameter "a" of the opening neck 20 in the reagent vial 18. Thus, the stopper 26 will be elastically deformed slightly upon insertion into the inner cylindrical surface 24 of the opening neck 20 to achieve a substantially leak-proof fit therewith. However, as will be explained further below, the dimensions of the stopper 26 enable slidable movement between the stopper 26 and the inner cylindrical surface 24 of the opening neck 20 in the reagent vial 18. This slidable movement enables selective disengagement of the stopper 26 to permit a flow of the reagent stored in the reagent vial 18 into the buffer solution stored in the reagent diluent container 12.

The container assembly 10 further comprises an adapter assembly 28. The adapter assembly 28 includes a unitarily molded coupler 30 and a unitarily molded retainer ring 32 which are selectively engageable with one another as explained herein. The coupler 30 and the retainer ring 32 may be molded from a suitable plastic material, such as a medium density polyethylene.

Figure 2:
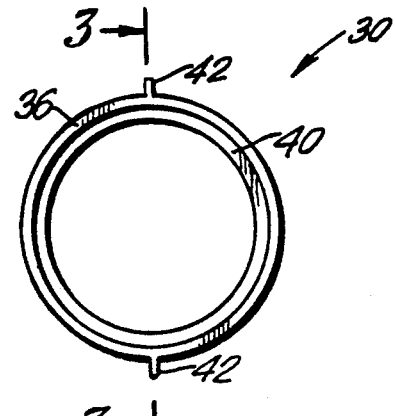
FIG. 2 is an end view of the coupler of the adapter assembly shown in FIG. 1

Turning to FIGS. 2 and 3, the coupler 30 comprises a generally cylindrical coupling collar 34 having opposed first and second ends 36 and 38. The first end 36 of the coupling collar 34 is characterized by an array of internal threads 40. The first end 36 is dimensioned to permit the internal threads 40. The first end 36 is dimensioned to permit the internal threads 40 thereof to be threadedly engaged with the external threads 16 on the opening neck 14 of the reagent diluent container 12. The first end 36 is further characterized by a pair of opposed teeth 41 and 42 extending generally radially outwardly from the first end 36. As will be explained further below, the teeth 41 and 42 define stops which engage with corresponding structure on the retainer ring 32 to prevent overengagement that could strip the threads formed thereon. The second end 38 of the coupling collar 34 is characterized by an array of external threads 44.

The coupler 30 further comprises a generally cylindrical hollow plunger 46 which extends internally from the coupling collar 34 at a location intermediate the ends 36 and 38 thereof, and which is unitarily joined to the coupling collar 34 by an annular internally disposed support 48. The hollow plunger 46 extends from the annular support 48 to a stopper engagement end 50 disposed beyond the second end 38 of the coupling collar 34. The hollow plunger 46 defines an external diameter "c" which is equal to or slightly less than the internal diameter "a" defined by the inner cylindrical surface 24 of the opening neck 20 on the reagent vial 18. Thus, the hollow plunger 46 can be slidably advanced in the opening neck 20 of the reagent vial 18 as explained further herein. As shown most clearly in FIG. 3, the relative radial dimensions of the coupling collar 34 and the plunger 46 define a generally annular space 52 therebetween. The annular space 52 is dimensioned to permit the opening neck 20 of the reagent vial 18 to be slidably inserted therein. The hollow plunger 46 may optionally be provided with openings 54 formed therein at selected locations either adjacent or slightly spaced from the stopper engagement end 50 thereof. The openings 54, if provided, may facilitate the flow of a reagent from the reagent vial 18 and through the hollow plunger 46 as explained below.

Figure 5:
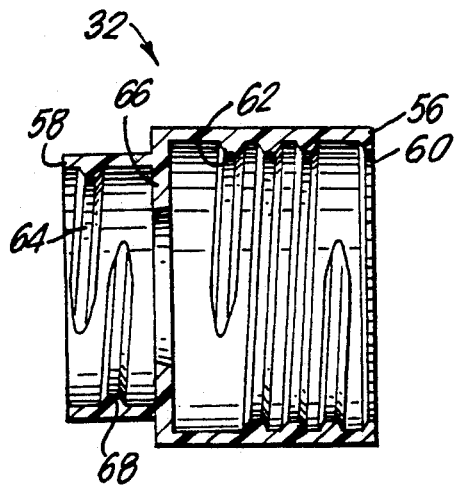
FIG. 5 is a cross sectional view taken along line 5—5 in FIG. 4.
Figure 4:
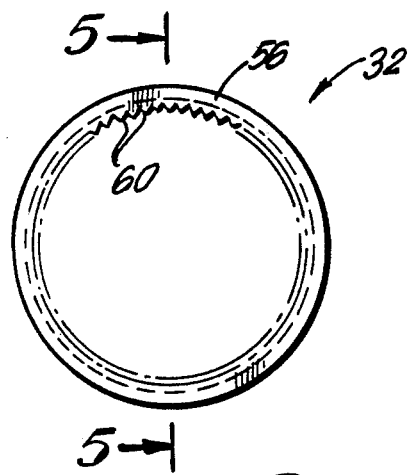
FIG. 4 is an end view of the retainer ring of the adapter assembly shown in FIG. 1.

The retainer ring 32, as illustrated in FIGS. 4 and 5 also is of generally cylindrical configuration. The retainer ring 32 defines opposed first and second ends 56 and 58 with a through aperture extending therebetween. The internal surface of the retainer ring 32 immediately adjacent the first end 56 thereof is defined by an array of locking teeth 60. The locking teeth 60 are disposed and dimensioned to engage the teeth 41 and 42 at the first end 36 of the coupling collar 34 on the coupler 30. The retainer ring 32 is characterized by first and second arrays of internal threads 62 and 64 adjacent the first and second ends 56 and 58 thereof respectively. The first end 56 is dimensioned such that the first array of internal threads 62 is threadably engageable with the external threads 44 adjacent the second end of the coupling collar 34 on the coupler 30. The second end 58 of the retainer ring 32 is dimensioned such that the second array of internal threads 64 is threadably engageable with the external threads 22 on the opening neck 20 of the reagent vial 18. The arrays of threads 16, 22, 40, 62 and 64 all are arranged such that rotation in a first direction will simultaneously achieve tightening of all components, and such that rotation in the opposite direction will simultaneously loosen all components. The interior of the retainer ring 32 is further characterized by an annular wall 66 disposed between the first and second arrays of internal threads 62 and 64. The annular wall 66 is further characterized by a circular opening 68 which is tapered to a wider opening on the portion thereof facing the first end 56 of the retainer ring 32. The opening 68 is dimensioned to receive the plunger 46 of the coupler 30, with the tapered configuration of the opening 68 functioning to guide the plunger 46 into the opening 68.

Figure 6:
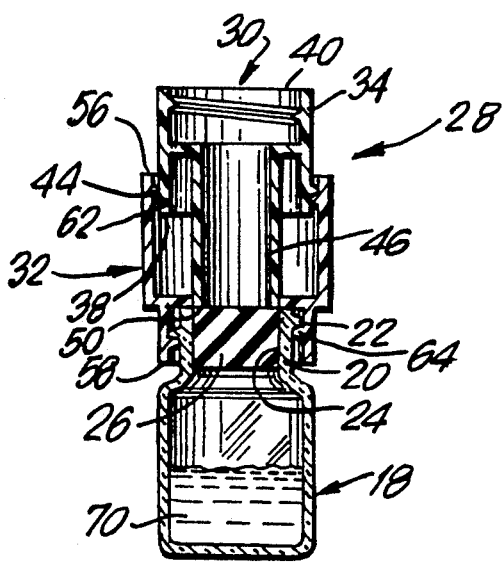
FIG. 6 is a cross sectional view of the adapter assembly mounted to a container prior to usage.

The adapter assembly 28 is employed initially as shown in FIG. 6. In particular, a reagent vial 18 having a reagent 70 stored therein is securely sealed with the stopper 26 urged into the inner cylindrical surface 24 of the opening neck 20. The adapter assembly 28 is then mounted to the reagent vial 18. In particular, the internal threads 64 at the second end 58 of the retainer ring 32 are threadedly engaged with the external threads 22 on the opening neck 20 of the reagent vial 18. The coupler 30 is then engaged to the retainer ring 32 in a first relative position. More particularly, the external threads 44 adjacent the second end 38 of the coupling collar 34 are threadedly engaged with the internal threads 62 adjacent the first end 56 of the retainer ring 32. The threaded engagement between the coupler 30 and the retainer ring 32 is such that the stopper engaging end 50 of the plunger 46 is either abutting or slightly spaced from the stopper 26 in the reagent vial 18. It will be appreciated that the coupler 30 and the retainer ring 32 can be initially engaged with one another in the relative position shown in FIG. 6 and then the initially assembled adapter assembly 28 may be mounted in their assembled form to the reagent vial 18. The sealed reagent vial 18 with the adapter assembly 28 mounted thereto can be assembled by the manufacturer of the reagent 70 at the place of manufacture, and can be shipped to a clinical chemical laboratory and stored for an extended duration in this sealed condition. Generally the manufacturer of the reagent will dispose an appropriate bar code or color code on the reagent vial 18 to identify the particular reagent stored therein. The same manufacturer of the reagent 70 may also provide the reagent diluent containers with an appropriate reagent buffer or diluent stored therein and with an easily removable seal (not shown) over the opening neck 14. Alternatively, the reagent buffer or diluent can be placed in the reagent buffer container 12 by the clinical chemical laboratory.

Figure 7:
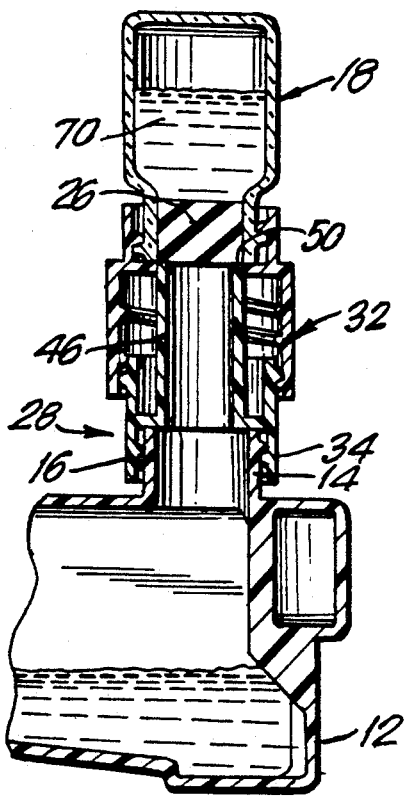
FIG. 7 is a cross sectional view showing the container assembly in a first operational condition.
Figure 8:
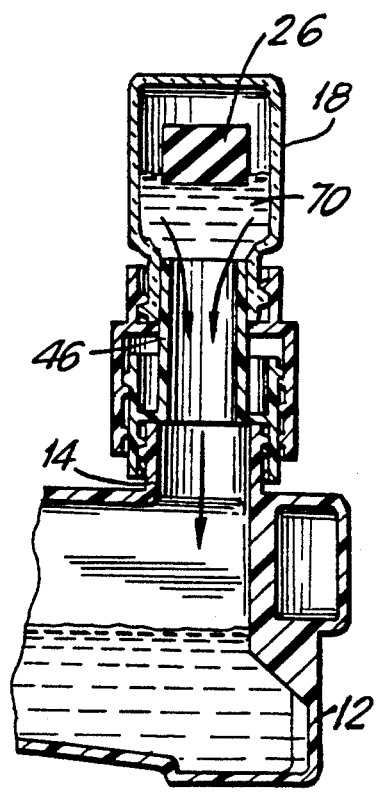
FIG. 8 is a cross sectional view similar to FIG. 7 container assembly in a second operational position.

The container assembly depicted in FIG. 1 is employed by the clinical chemical laboratory as illustrated in FIGS. 7 and 8. In particular, shortly prior to conducting an appropriate diagnostic test, a laboratory technician will match a reagent vial 18 having an adapter assembly 28 thereon with a reagent diluent container 12 having a diluent or buffer solution 72, contained therein. The reagent vial 18 and the diluent container 12 may be color coded to ensure a proper match for a particular diagnostic test. Alternatively the technician may add an appropriate diluent solution 72 to an empty container 12. The technician then will invert the combined reagent vial 18 and adapter assembly 28 depicted in FIG. 6 and mount the first end 36 of the coupler 30 to the reagent diluent container 12. More particularly, the internal threads 40 on the coupling collar 34 are threadedly engaged with the external threads 16 on the opening neck 14 of the reagent diluent container 12. This initially engaged orientation is depicted in FIG. 7. The lab technician will then continue to exert rotational forces on the reagent vial 18 to cause additional threaded engagement of the coupler 30 with the retainer ring 32. This additional threaded engagement will urge the engaging end 50 of the plunger 46 into the stopper 26, and will forcibly urge the stopper 26 into the reagent vial 18 as shown in FIG. 8. The stopper 26 will effectively pop free of the inner cylindrical surface 24 of the reagent vial 18 and will forcibly move away from the opening neck 20. This rapid movement of the stopper 26 within the reagent vial 18 will create a turbulence within the reagent 70 that will urge the reagent 70 through the hollow plunger 46 and into the diluent solution 72 stored in the reagent diluent container 12. As noted above, the plunger 46 may be provided with apertures or irregular configurations adjacent the engagement end 50 to positively ensure a flow of the reagent 70 through the plunger 46 even in the unlikely event that the stopper 26 will precisely seat itself onto the end of the plunger 46.

In summary, an assembly of containers is provided including a reagent diluent container and a reagent vial which are selectively engageable with an adapter assembly. The adapter assembly includes a plunger that is advanceable toward the seal of the reagent vial to displace the seal and enable a flow of the reagent into the reagent diluent container. The adapter assembly preferably comprises a coupler and a retainer ring that are threadedly engageable with one another. The coupler is threadedly engageable to the reagent diluent container, while the retainer ring is threadedly engageable with the reagent vial. The various arrays of threads are oriented such that a rotation of the reagent vial will generate a simultaneous tightening of all threadedly engaged components to ensure simple yet effective advancement of the plunger on the coupler into the seal of the reagent vial.

While the invention has been described with respect to a preferred embodiment, it is apparent that various changes can be made without departing from the scope of the invention as defined by the appended claims. In particular, the respective containers can be of configurations other than those illustrated herein. Additionally, the hollow plunger of the adapter assembly can take various configurations depending upon the flow characteristics of the reagent and the configuration of the seal or stopper. Similarly, the seal of the reagent vial may take many other configurations than the preferred stopper illustrated herein. Furthermore, in certain embodiments the adapter assembly may be initially mounted to the reagent diluent container and the sealed reagent vial may be threadedly engaged therewith. Other similar variations will be apparent to the person having skill in this art after having read the above description.

We claim:

1. A method for mixing a controlled amount of a concentrated reagent with a diluent prior to performing a diagnostic test therewith, said method comprising the steps of:

providing a reagent vial having sidewalls and an opening, wherein said sidewalls and said opening are molded together as a one-piece unit and having the reagent stored therein, and a selectively displaceable seal extending across the opening and sealingly engaging said opening;

providing a diluent container having an opening and having a diluent stored therein;

providing an adapter having opposed mounting means for selective mounting to the openings of the reagent vial and the diluent container, a plunger in spaced relationship to the mounting means for selective displacement of the entire seal, of the reagent vial, and communication means for enabling material flow readily back and forth through the adapter;

mounting the adapter to the reagent vial such that the plunger is in proximity to the seal of the reagent vial;

mounting the adapter to the opening of the diluent container; and moving the reagent vial relative to the diluent container such that the plunger displaces the entire seal of the reagent vial to permit mixing of the reagent and the diluent.

2. A method as in claim 1 wherein the method comprises the further step of storing the reagent after the mounting of the adapter thereto.

3. A method as in claim 1 wherein the method includes the further step of storing the reagent prior to mounting the adapter thereto.

4. A method as in claim 1 wherein the adapter comprises a retainer ring and a coupler threadedly engageable with one another, and wherein the step of moving the reagent vial relative to the diluent container comprises threadedly advancing the retainer ring and the coupler relative to one another.

5. A method as in claim 4 wherein the coupler is threadedly engageable with the diluent container, and wherein rotatable movement of the retainer ring initially mounts the coupler to the diluent container and subsequently advances the retainer ring onto the coupler such that the plunger displaces the entire seal of the reagent vial.

* * * * *